(12) United States Patent
Rizoiu et al.

(10) Patent No.: US 6,567,582 B1
(45) Date of Patent: May 20, 2003

(54) FIBER TIP FLUID OUTPUT DEVICE

(76) Inventors: Ioana M. Rizoiu, 1330 Pavoreal, San Clemente, CA (US) 92673; Jeffrey W. Jones, 12898 St. Highway 410, Robertson, WY (US) 82944

( * ) Notice: Subject to any disclaimer, the term of this patent is extended or adjusted under 35 U.S.C. 154(b) by 0 days.

(21) Appl. No.: 09/822,981

(22) Filed: Mar. 30, 2001

Related U.S. Application Data (63) Continuation-in-part of application No. 09/469,571, filed on Dec. 22, 1999, now Pat. No. 6,389,193, and a continuation-in-part of application No. 09/256,697, filed on Feb. 24, 1999, now Pat. No. 6,350,123, which is a continuation-in-part of application No. 08/985,513, filed on Dec. 5, 1997, now abandoned, which is a continuation of application No. 08/522,503, filed on Aug. 31, 1995, now Pat. No. 5,741,247, and a continuation-in-part of application No. 08/995,241, filed on Dec. 17, 1997, now abandoned, which is a continuation of application No. 08/575,775, filed on Dec. 20, 1995, now Pat. No. 5,785,521.

(60) Provisional application No. 60/113,293, filed on Dec. 22, 1998.

(51) Int. Cl.[7] ............................. G02B 6/26; A61C 19/06
(52) U.S. Cl. ............................ 385/25; 385/31; 433/31; 604/20; 604/82; 362/572
(58) Field of Search ............................ 385/15, 25, 53, 385/115, 117, 118, 134, 147, 902; 362/554, 562, 572–575, 580; 604/20, 21, 82, 83; 433/31

(56) References Cited

U.S. PATENT DOCUMENTS

| | | | | |
|---|---|---|---|---|
| 3,851,650 A | * | 12/1974 | Darling | 604/129 |
| 4,175,545 A | * | 11/1979 | Termanini | 604/21 X |
| 4,330,274 A | * | 5/1982 | Friedman et al. | 433/29 |
| 5,354,294 A | * | 10/1994 | Chou | 606/16 |
| 5,476,379 A | * | 12/1995 | Disel | 433/29 |
| 5,669,769 A | * | 9/1997 | Disel | 433/29 |
| 5,738,666 A | * | 4/1998 | Watson et al. | 604/264 |

* cited by examiner

*Primary Examiner*—John D. Lee (57) ABSTRACT

A fiber tip fluid output device is provided for holding a fiber tip in an electromagnetic energy cutting apparatus and for directing water particles over a radiation delivery end of the fiber tip. The output device includes a generally cylindrical body having an outer surface, a proximal end, a distal end, and a lumen extending therebetween. The lumen is sized and shaped to accommodate a fiber tip therethrough so that the fiber tip extends through the lumen. The device further includes a plurality of apertures extending around the generally cylindrical body, with each of the apertures fluidly connecting the outer surface to the lumen. Fluid is mixed around the cylindrical body, before entering the lumen through the apertures for additional mixing. The mixed fluid is then output from the lumen onto the fiber tip, for subsequent interaction with electromagnetic energy in an interaction zone above a target surface.

53 Claims, 7 Drawing Sheets

FIBER TIP FLUID OUTPUT DEVICE

This application is a continuation-in-part of U.S. application Ser. No. 09/469,571, filed Dec. 22, 1999, now U.S. Pat. No. 6,389,193 which is commonly assigned and the contents of which are expressly incorporated herein by reference. This application is a also a continuation-in-part of U.S. application Ser. No. 09/256,697, filed Feb. 24, 1999, now U.S. Pat. No. 6,350,123, which is commonly assigned and the contents of which are expressly incorporated herein by reference. U.S. application Ser. No. 09/256,697 is a continuation-in-part of U.S. application Ser. No. 08/985,513, filed Dec. 5, 1997, now abandoned, which is a continuation of U.S. application Ser. No. 08/522,503, filed Aug. 31, 1995, (now U.S. Pat. No. 5,741,247), and is a continuation-in-part of U.S. application Ser. No. 08/995,241, filed Dec. 17, 1997, now abandoned, which is a continuation of U.S. application Ser. No. 8/575,775, filed Dec. 20, 1995, (now U.S. Pat. No. 5,785,521), the contents of which are expressly incorporated herein by reference. The benefit under 35 U.S.C. 119(e) of U.S. provisional application 60/113,293, filed on Dec. 22, 1998, is also hereby claimed.

BACKGROUND OF THE INVENTION

1. Field of the Invention

The present invention relates to handpieces for delivering electromagnetic radiation.

2. Description of the Related Art

Handpieces have existed in the prior art for delivering electromagnetic radiation.

SUMMARY OF THE INVENTION

The rotating handpiece of the present invention includes a fiber tip fluid output device and a removable trunk fiber optic. The trunk fiber optic and the fiber tip are disposed perpendicularly, with a parabolic mirror disposed there between. Slight misalignments of the trunk fiber optics, as well as imperfections on the output surface of the fiber optic, are compensated by the parabolic mirror which consistently and efficiently focuses the electromagnetic energy into the input end of the fiber tip. Moreover, in accordance with one aspect of the present invention, the handpiece can be rotated about the longitudinal axis of the trunk fiber optic, with the parabolic mirror continuing to efficiently couple the electromagnetic energy from the trunk fiber optic into the fiber tip.

In accordance with one aspect of the present invention, a fiber tip fluid output device is provided for holding a fiber tip in an electromagnetic energy cutting apparatus and for directing water particles over a radiation delivery end of the fiber tip. The fiber tip fluid output device comprises a generally cylindrical body having an outer surface, a proximal end, a distal end, and a lumen extending between the proximal end and the distal end, the lumen being sized and shaped to accommodate a fiber tip therethrough so that the fiber tip extends through the lumen from the proximal end to the distal end of the generally cylindrical body. The fiber tip fluid output device further comprises a plurality of apertures extending around the generally cylindrical body, wherein each of the apertures of the plurality of apertures fluidly connects the outer surface to the lumen. Fluid is mixed around the cylindrical body, before entering the lumen through the plurality of apertures for additional mixing. The mixed fluid is then output from the lumen of the fiber tip fluid output device onto the fiber tip, for subsequent interaction with electromagnetic energy in an interaction zone above a target surface.

The present invention, together with additional features and advantages thereof, may best be understood by reference to the following description taken in connection with the accompanying illustrative drawings.

DETAILED DESCRIPTION OF THE PRESENTLY PREFERRED EMBODIMENTS

Figure 1:
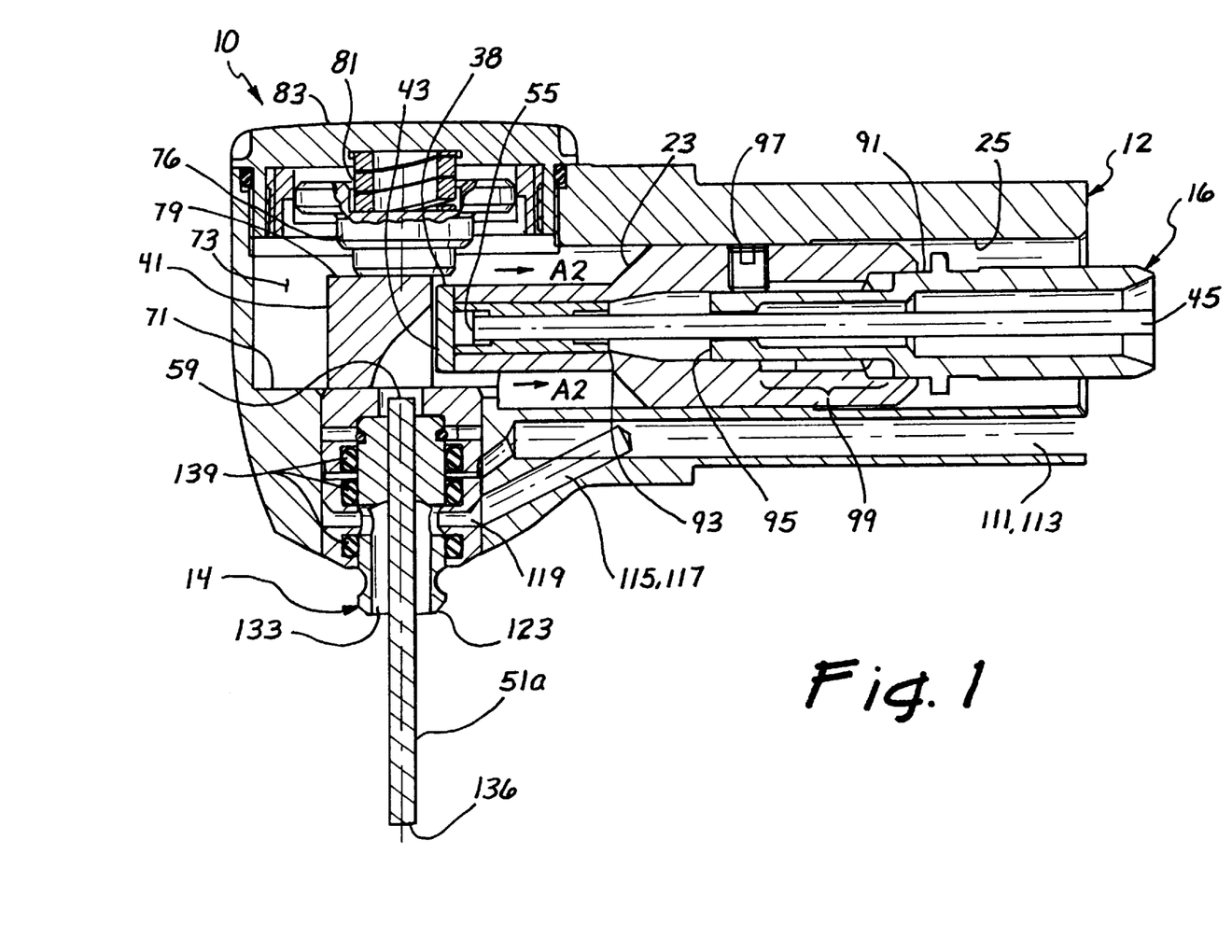
FIG. 1 is a cross sectional view of the rotating handpiece in accordance with the presently preferred embodiment.

Referring more particularly to the drawings, FIG. 1 illustrates a cross sectional view of the rotating handpiece 10. The rotating handpiece comprises a handpiece head 12, a fiber tip fluid output device 14, and a removable trunk fiber assembly 16. These components can be seen in a partially disassembled state in FIG. 3, wherein the axis 18 of the removable trunk fiber assembly 16 is aligned with the axis 20 of the handpiece head 12 for insertion into the handpiece head 12. Once the axis 18 of the removable fiber assembly 16 is aligned with the axis 20 of the handpiece 12, the removable trunk fiber assembly 16 is moved in the direction of the arrow A1 into the handpiece head 12, while the axes 18 and 20 are maintained in approximate alignment. The contacting surface of the outer surface of the chuck 23 engages the inner surface 25 of the rotating handpiece 10, to thereby ensure alignment of the axis 18 of the removable trunk fiber assembly 16 and the axis 20 of the handpiece head 12. As the removable trunk fiber assembly 16 is inserted further in the direction A1 into the handpiece 12, the abutting surface 28 engages with a corresponding abutting surface (not shown) within the collar 31 of the handpiece head 12. The corresponding abutting surface 28 preferably snaps with the abutting surface 31, as the removable trunk fiber assembly 16 is fully inserted into the handpiece head 12. Any type of locking engagement between the abutting surface 28 and a corresponding abutting surface within the collar 31, as known in the art, may be used to ensure that the removable trunk fiber assembly 16 is always inserted the same distance into the handpiece head 12. As shown in FIG. 1, the distal tip 38 of the removable trunk fiber assembly 16 is brought into close proximity with the parabolic mirror 41. In the presently preferred embodiment, the distal tip 38 of the removable trunk fiber assembly 16 comprises a window 43 for protecting the trunk fiber optic 45 from contaminants, such as water. In the alternative embodiment shown in FIG. 2, the distal tip 38a is not protected with a window. As shown in FIG. 1, the fiber tip 51 of the fiber tip fluid output device 14 is also accurately placed in close proximity to the parabolic mirror 41. A loading tool 17 is preferably used to assist in the placement of the fiber tip fluid output device 14 into the handpiece head 12, as discussed below with reference to FIGS. 5 and 7–9. Electromagnetic energy exiting from the output end 55 of the trunk fiber optic 45 is collected by the parabolic mirror 41 and, subsequently, reflected and focused onto the input end 59 of the fiber tip 51.

Figure 4A:
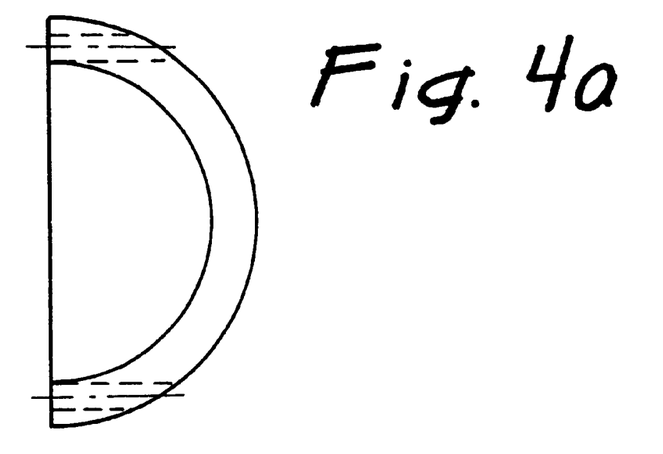
Figure 4B:
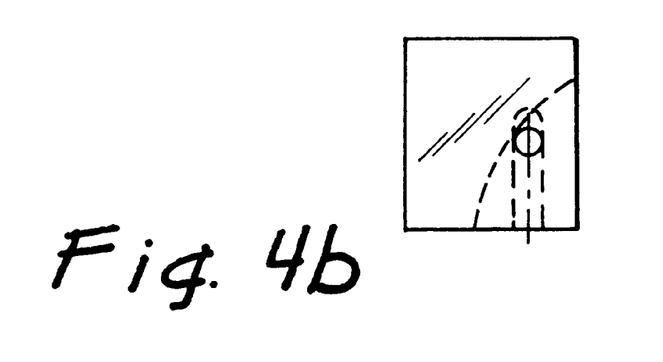
Figure 4C:
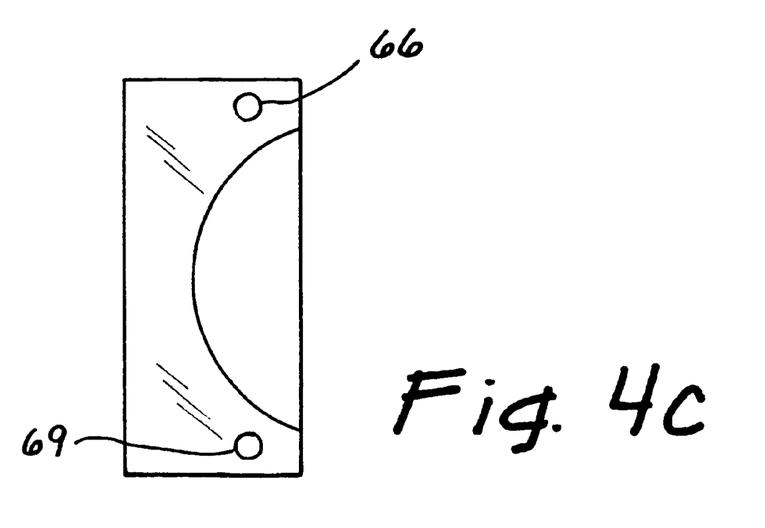

In the presently preferred embodiment, the electromagnetic energy exiting from the output end 55 of the trunk fiber optic 45 comprises a wavelength on the order of 3 mm. The material of the parabolic mirror 41 is selected to provide an efficient reflection and focusing into the input end 59. As presently embodied, the electromagnetic energy is generated from an Er:YSGG laser, and the material of the parabolic mirror 41 comprises a gold plating to provide reflectivity of approximately 99.9 percent. Other materials may be selected in accordance with design parameters. Other reflective surfaces and materials for the parabolic mirror 41 may be selected, in accordance with the laser being used and the desired efficiency of reflection. For example, if a lower reflectivity is selected, then additional cooling may be needed for the parabolic mirror 41 (such as a greater flow rate of cooled and/or filtered air across the surface of the parabolic mirror 41). FIGS. 4a, 4b and 4c illustrate various views of the parabolic mirrors 41 of the presently preferred embodiment. The flat surface of the parabolic mirror 41, which is closest to the fiber tip 51, is preferably provided with two recessed areas 66 and 69. These two recessed areas mate with corresponding protrusions (not shown) on the floor 71 of the internal chamber 73 of the handpiece head 12. A spring loaded plunger 76 presses against the upper surface 79 of the parabolic mirror 41 under the pressure of the spring 81. A screw cap 83 holds the spring 81 against the spring loaded plunger 76. The combination of the spring loaded plunger 76, the recessed areas 66,69 of the parabolic mirror 41, and the corresponding protrusions on the floor 71, together, accurately align the parabolic mirror 41 for efficient coupling of electromagnetic energy between the output end 55 of the trunk fiber optic 45 and the input end 59 of the fiber tip 51. In modified embodiments, either or both of the output end 55 of the trunk fiber optic 45 and the input end 59 of the fiber tip 51 is/are provided with an anti-reflective coating. Although it is preferred to have the trunk fiber optic 45 perfectly aligned in relation to the parabolic 41 and the fiber tip 51, the alignment between these three elements is seldomly perfect. In the presently preferred embodiment, the misalignment of the axis of the trunk fiber optic 45 and the axis of the fiber tip 51 is within plus or minus 1 percent error.

In a modified embodiment, a pentaprism (five-sided prism) is used instead of the parabolic mirror 41 for coupling the trunk fiber optic 45 to the fiber tip 51.

In addition to slight misalignment of the axis of the trunk fiber optic 45, slight imperfections on the output end 55 of the trunk fiber optic 45 may also be present. The parabolic mirror 41 corrects for both of these slight errors, by collecting the electromagnetic energy from the output end 55 of the front fiber optic 45 and, subsequently, focusing the electromagnetic energy into the input end 55 of the fiber tip 51.

The parabolic mirror 41 may also comprise molypdium, in a preferred embodiment.

The clamp assembly 91 operates to firmly grip and hold the trunk fiber optic 45. In the presently preferred embodiment, the clamp assembly 91 is provided with at least one slit, which extends from the distal end 93 of the clamp assembly 91 to a region 95 just distal of the set screw 97. As presently embodied, the at least one slit extending from the distal end 93 to the region 95 just distal of the set screw 97 comprises two slits, which are adapted to allow the clamp assembly 91 to be compressed by the chuck 23 onto the trunk fiber optic 45. The chuck 23 thus presses against the portion of the clamp assembly 91, wherein the portion is defined between the distal end 93 and the region 95, to thereby have the clamp assembly 91 squeeze and hold the trunk fiber optic 45 in place. In the presently preferred embodiment, the set screw 97 is used to hold the chuck 23 in place and prevent rotation thereof. In the illustrated embodiment, the outer surface of the clamp assembly 91 is provided with threads 99 for engaging with corresponding threads on the inner surface of the chuck 23. In the presently preferred embodiment, the chuck 23 is screwed onto the threads of the clamp assembly 91, before the removable trunk fiber assembly 16 is inserted into the handpiece 12. The chuck 23 is screwed onto the clamp assembly 91 to a predetermined tightness, and then the set screw 97 is secured thereto to securely hold the chuck 23 to the clamp assembly 91. Subsequently, the removable trunk fiber assembly 16 is inserted and secured into the handpiece head 12.

Referring to FIGS. 5 and 7–9, the fiber tip fluid output device 14 comprises a generally cylindrical body having an outer surface, a proximal end, a distal end, and a lumen extending between the proximal end and the distal end. The lumen is sized and shaped to accommodate the fiber tip 51a therethrough so that the fiber tip 51a extends through the lumen from the proximal end to the distal end of the generally cylindrical body. The fiber tip fluid output device 14 further comprises a plurality of apertures 125 extending around the generally cylindrical body. Each of the apertures 125 fluidly connects the outer surface to the lumen. As presently embodied, the lumen comprises a first diameter near the proximal end and a second diameter near the distal end, wherein in the illustrated embodiment the second diameter is greater than or equal to about two times the first diameter. As presently embodied, the lumen comprises a proximal lumen section and a distal lumen section, the proximal lumen section having a diameter which in the illustrated embodiment is equal to the first diameter and the distal lumen section having a diameter which in the illustrated embodiment is equal to the second diameter. The proximal lumen section comprises a proximal end, a distal end, and a lumen axis extending between the proximal end and the distal end; the distal lumen section comprises a proximal end, a distal end, and a lumen axis extending between the proximal end and the distal end; and the diameter of the proximal lumen section in the illustrated embodiment is preferably substantially constant along a length of the proximal lumen section between the proximal end of the proximal lumen section and the distal end of the proximal lumen section. The diameter of the distal lumen section is preferably substantially constant along a length of the distal lumen section between the proximal end of the distal lumen section and the distal end of the distal lumen section. In the illustrated embodiment, the first diameter transitions to the second diameter at the distal end of the proximal lumen section and the proximal end of the distal lumen section, a distal opening of the fiber tip fluid output device 14 has a diameter which is equal to the second diameter, and a proximal opening of the fiber tip fluid output device 14 has a diameter which is equal to the first diameter. In the illustrated embodiment, each of the apertures 125 has a diameter which is about half of the first diameter.

Figures 5A, 5B:
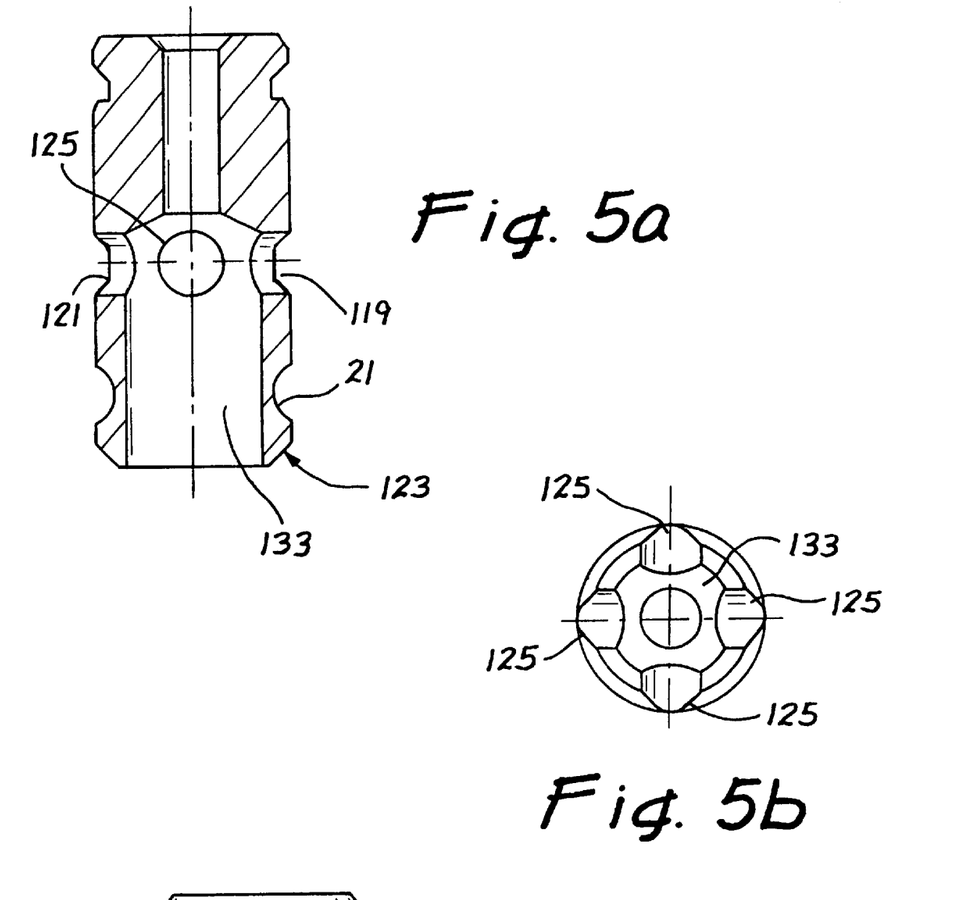
Figure 5C:
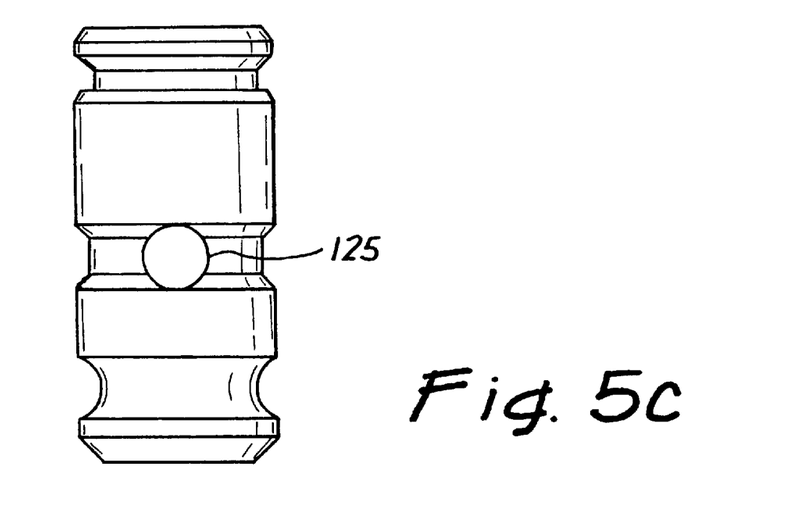

The apertures 125 are preferably disposed within a first depression 121. A second depression extends around the generally cylindrical body near the proximal end, and a third depression extends around the generally cylindrical body near the distal end, wherein the first depression is disposed about half way between the second depression and the third depression in the illustrated embodiment. As presently embodied, the distal lumen section tapers into the proximal lumen section along a length of the lumen that in the illustrated embodiment is equal to about one third of at least one of the cross-sectional diameters of the apertures 125.

The rotating handpiece 10 of the presently preferred embodiment preferably uses the electromagnetically induced cutting system disclosed in U.S. Pat. No. 5,741,247, the entire contents of which are expressly incorporated herein by reference. For example, an engineered and controllable atomized distribution of fluid particles is placed into an interaction for absorption of electromagnetic energy (from the fiber tip 51a) and for subsequent expansion to impart mechanical cutting forces onto a target surface. In the illustrated embodiment of FIG. 1, separate air and fluid lines 111, 113, which may be similar to those described in U.S. Pat. No. 5,741,247, run parallel to one another in the distal direction toward the feed channels 115, 117. In other embodiments, the air and fluid lines 111, 113 may comprise a first fluid line for carrying a first fluid and a second fluid line for carrying a second fluid, and further may comprise one or more additional fluid lines (not shown). Thus, while the illustrated embodiment describes the first fluid being air and the second fluid being water, the present disclosure is not limited to such structure and use. For example, the first and second fluids, and additional fluids, may comprise any of the components described in U.S. Pat. No. 5,785,521, the entire contents of which are expressly incorporated herein by reference. Some or all of the components of U.S. Pat. No. 5,785,521 may be premixed and carried through fluid lines, such as the lines 115, 117, or not premixed and mixed within the circumferential chamber 119 discussed below. The feed channels 115, 117, carrying a supply of air and water, respectively, as presently embodied, feed into circumferential chamber 119. Referring to FIGS. 5a–5c, the circumferential chamber 119 is preferably formed in a first depression 121 of the fiber tip ferrule 123. In an alternative embodiment, the section 121 may not have any depression.

As can be seen from FIG. 5b, for example, four apertures 125 are disposed in the first depression 121 of the fiber tip ferrule 123. In modified embodiments, other numbers of apertures may be incorporated. Air traveling into the circumferential chamber 119 from the feed channel 115, and water traveling into the circumferential chamber 119 from the feed channel 117, are both initially mixed in the circumferential chamber 119. In one embodiment, the first and second fluids may comprise air and a medicated or flavored water, and in another embodiment the first and second fluids may comprise water and at least one other fluid. In still another embodiment, at least one of the first and second fluids may comprise a medicament, such as chlorhexidine gluconate.

The initially-mixed air and water travel from the circumferential chamber 119 through the orifices 125 and into the lumen 133. The air and water is further mixed and atomized within the lumen 133. The atomized water under air pressure subsequently travels along the fiber tip 51 in a direction toward the output end 136 of the fiber tip 51. In a preferred embodiment, the fiber tip 51a is permanently affixed to and extends through the fiber tip fluid output device 14. As presently embodied, three O-ring seals 139 are provided to seal the inside of the rotating handpiece from the air and water.

Figure 7:
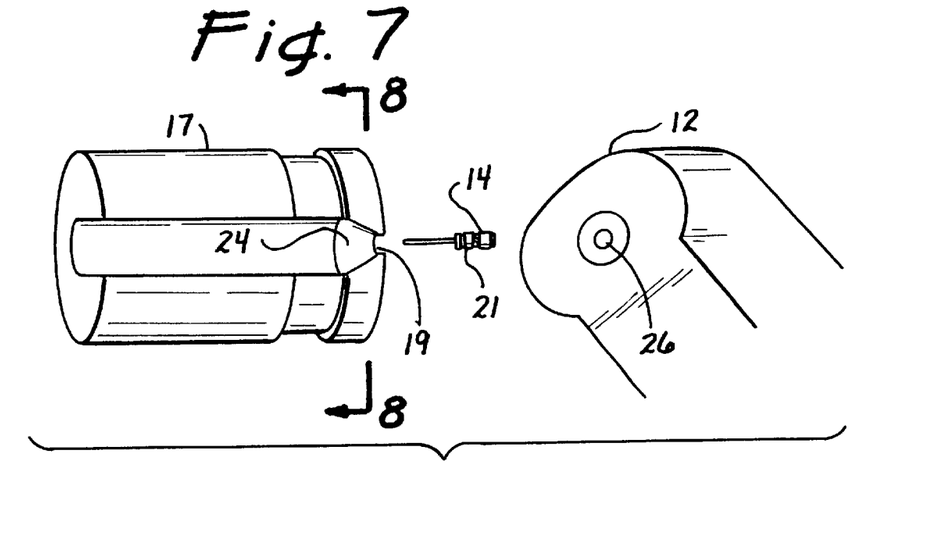
FIG. 7 is a perspective view of the loading tool, fiber tip fluid output device, and handpiece head in a disassembled configuration.
Figure 8:
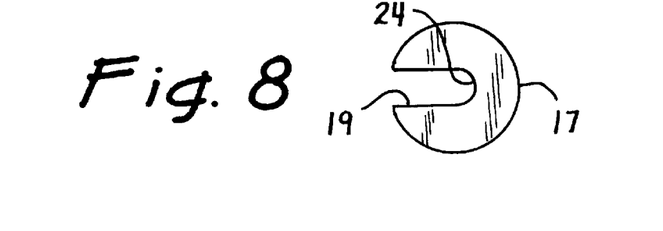
FIG. 8 is an end view of the loading tool, taken along the line 8—8 of FIG. 7.

FIG. 7 illustrates the loading tool 17, the fiber tip fluid output device 14, and handpiece head 12 in a disassembled configuration, and FIG. 8 is an end view of the loading tool 17, taken along the line 8—8 of FIG. 7.

Figure 9:
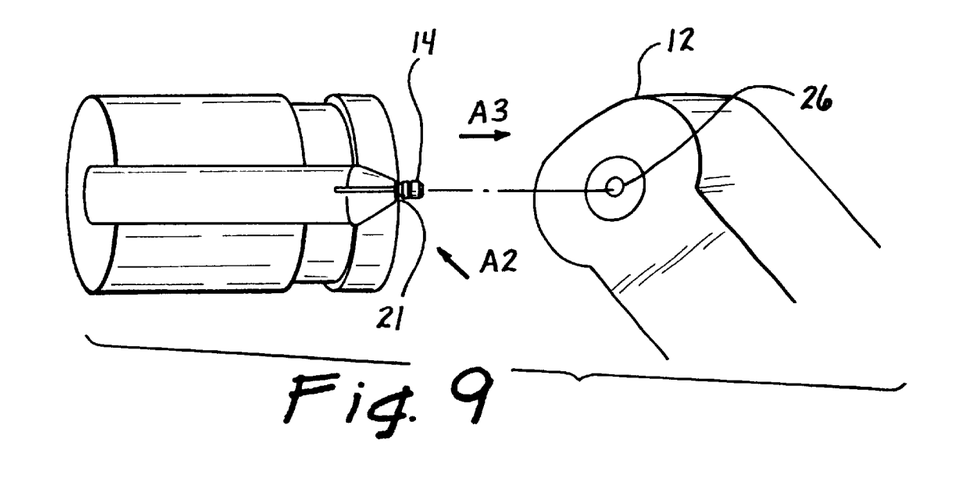
FIG. 9 is a perspective view of the fiber tip fluid output device partially secured onto the loading tool, just before insertion of the fiber tip fluid output device into the handpiece head.

FIG. 9 shows the fiber tip fluid output device 14 partially secured onto the loading tool 17. The proximal end of fiber tip fluid output device 14 is preferably gripped by the hand of a user and slid into the slot 19 of the loading tool 17 in the direction of the arrow A2. As presently embodied slot 19 fits around the third depression 21 of the fiber tip fluid output device 14, and the fiber tip fluid output device 14 is slid within the slot 19 in the direction of the arrow A2 until the fiber tip fluid output device 14 reaches the end 24 of the slot 19. The loading tool is then advanced in the direction of the arrow A3 to firmly secure the fiber tip fluid output device 14 into the orifice 26 of the handpiece head 12. The loading tool 17 is then removed from the fiber tip fluid output device 14 to leave the fiber tip fluid output device 14 firmly secured within the orifice 26. As presently embodied, a width of the slot 19 is slightly larger than a diameter of the third depression 21, so that the fiber tip fluid output device 21 can be removably and snugly held by the loading tool 17.

Figure 2:
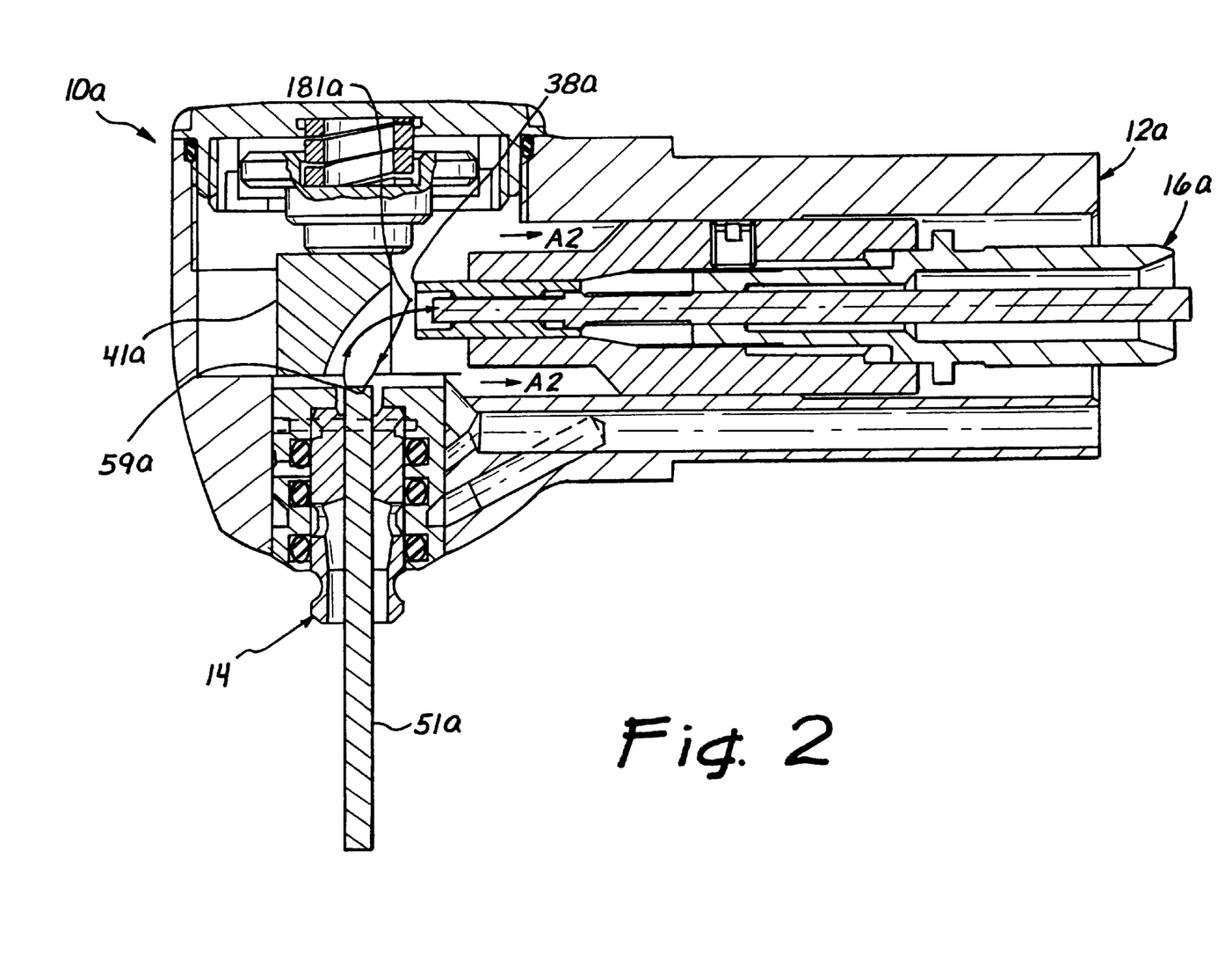
FIG. 2 is a cross sectional view of an alternative embodiment of the rotating handpiece.
Figure 3:
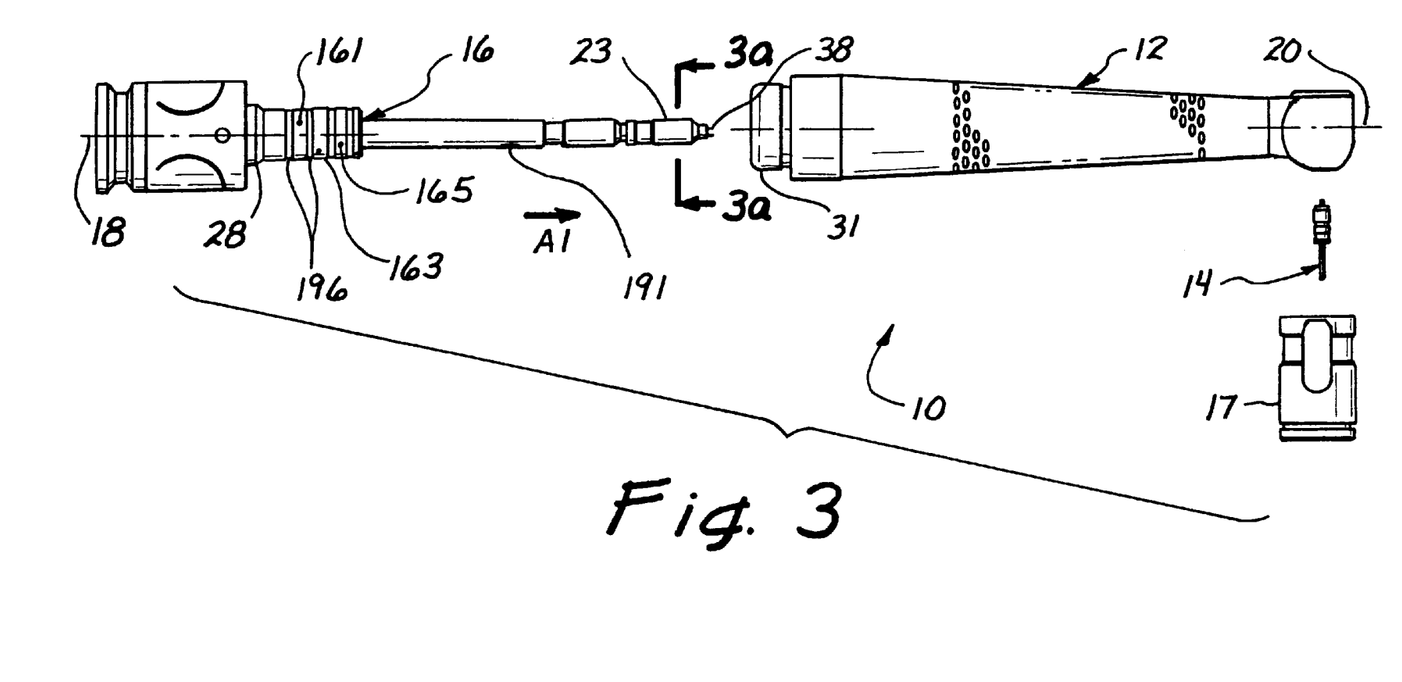
FIG. 3 is a side elevation view of the rotating band piece in a partially disassembled state.
Figure 3A:
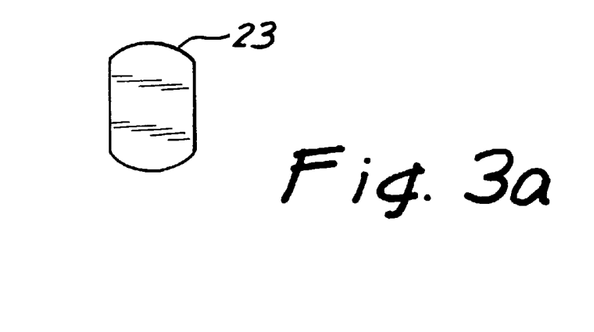
FIGS. 3a, 4a–4c, 5a–5c, 6a and 6b are other views of the invention.

Referring to FIG. 3, the removable trunk fiber assembly 16 is preferably provided with three radial ports for introducing air, water, and (optionally) cooling air. More particularly, a fluid radial channel 161 feeds fluid (e.g., water) into the fluid channel 111, an air radial channel 163 feeds air into the air channel 113, and an optional cooling-air radial channel 165 feeds cooling air along a cooling-air channel, which exits in close proximity to the parabolic mirror 41. In a preferred embodiment, the exit angle of the cooling air channel directs cooling air directly onto the parabolic mirror 41, so that the cooling air is reflected from the parabolic mirror 41 onto the input end 59 of the fiber tip 51 and, subsequently, onto the window 43. In FIG. 2, the cooling air exits from an orifice 181a and is channeled directly onto the input end 59a of the fiber tip 51a. Subsequently, the air is directed onto the parabolic mirror 41 and reflected onto the output end 55 of the trunk fiber optic 45. This configuration could also be implemented for the system of FIG. 1, wherein the cooling air subsequently is directed onto the window 43. Alternatively, in the embodiment of FIG. 2, the cooling air exiting the orifice 181a can be channeled directly onto the parabolic mirror 41, focusing onto the input end 59a of the fiber tip 51. In the embodiments of both FIG. 1 and FIG. 2, the cooling air is subsequently channeled in the direction of the arrows A2 through channels formed in the chuck 23. As shown in FIG. 3a, the chuck 23 preferably has portions of its two sides removed, to thereby form channels for passage of the cooling air. The cooling air travels through the channels of the chuck 23 under a vacuum pressure and, subsequently, is drawn into a removal port 191. Upon entering the removal port 191 under the vacuum, the cooling air travels in a direction opposite to the arrow A1 and exits the removal trunk fiber assembly 16. The four O-rings 196 insulate the radial channels 161, 163, 165 from one another.

Figures 6A, 6B:
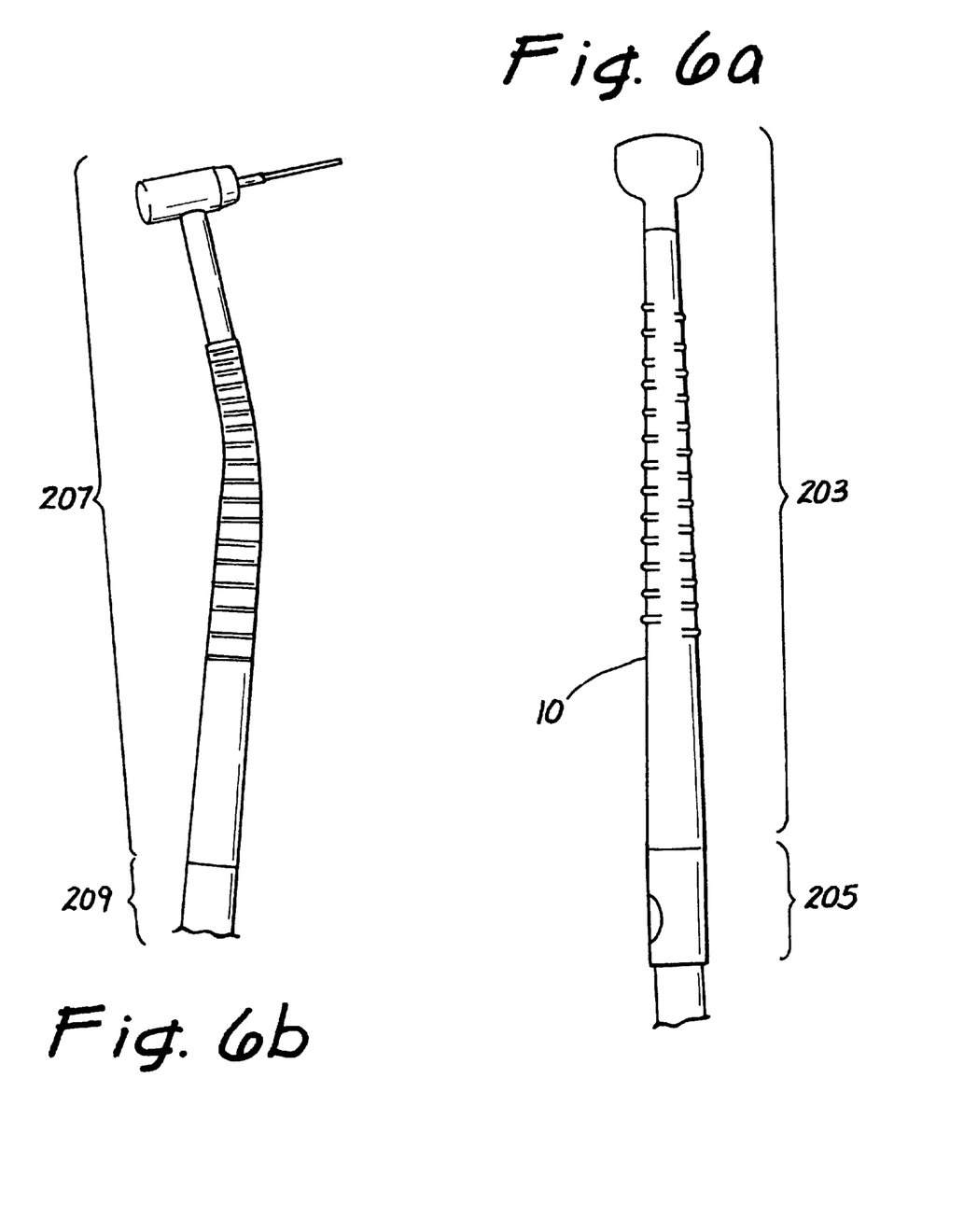

FIG. 6a illustrates a side elevation view of the assembled rotating handpiece 10 and FIG. 6b illustrates a modified embodiment of the rotating handpiece 10, wherein the neck is slightly bent. In FIGS. 6a the portion indicated by reference numeral 203 is adapted to rotate about an axis of the rotating handpiece 10. The portion 205 does not rotate. Similarly, in FIG. 6b, the portion 207 is adapted to rotate about an axis of the rotating handpiece, and the portion 209 docs not rotate. In the embodiment of FIG. 6b, the trunk fiber optic is configured to be slightly flexible, since the trunk fiber optic will need to bend and flex as the portion 207 is rotated relative to the portion 209. In either of the embodiments of FIGS. 6a and 6b, the user holds the rotating portion (203 or 207) with his or her thumb and two fingers (such as is conventional in the art) and allows the stationary portion (205 or 209) to rest on a portion of the hand bridging the user's forefinger and thumb. The three fingers holding the rotating portion (203 or 207) contact the rotating portion and can rotate the rotating portion, as the fixed portion (205 or 209) does not rotate and rests on the portion of the hand bridging the hand and the forefinger. Although an exemplary embodiment of the invention has been shown and described, many other changes, modifications and substitutions, in addition to those set forth in the above paragraphs, may be made by one having ordinary skill in the art without necessarily departing from the spirit and scope of this invention.

What is claimed is:

1. A fiber tip fluid output device for holding a fiber tip in an electromagnetic energy cutting apparatus and for directing fluid particles over a radiation delivery end of the fiber tip, the fiber tip fluid output device comprising:
a generally cylindrical body having an outer surface, a proximal end, a distal end, and a lumen extending between the proximal end and the distal end, the lumen being sized and shaped to accommodate a fiber tip therethrough so that the fiber tip extends through the lumen from the proximal end to the distal end of the generally cylindrical body; and
a plurality of apertures extending around the lumen of the generally cylindrical body, each of the apertures of the plurality of apertures fluidly connecting the outer surface to the lumen.

2. The fiber tip fluid output device as set forth in claim 1, and further comprising a depression disposed in the outer surface of the generally cylindrical body, the depression extending around the generally cylindrical body and serving as a mixing chamber for mixing fluids together when the fiber tip fluid output device is connected to the electromagnetic energy cutting apparatus.

3. The fiber tip fluid output device as set forth in claim 2, wherein the lumen comprises a first diameter near the proximal end and a second diameter near the distal end, the first diameter being different from the second diameter.

4. The fiber tip fluid output device as set forth in claim 3, wherein the second diameter is greater than or equal to about two times the first diameter.

5. The fiber tip fluid output device as set forth in claim 3, wherein a distal opening of the fiber tip fluid output device has a diameter which is equal to the second diameter and a proximal opening of the fiber tip fluid output device has a diameter which is equal to the first diameter.

6. The fiber tip fluid output device as set forth in claim 3, wherein each aperture has a diameter which is about half of the first diameter.

7. The fiber tip fluid output device as set forth in claim 2, wherein the lumen comprises a proximal lumen section and a distal lumen section, the proximal lumen section having a diameter which is equal to the first diameter and the distal lumen section having a diameter which is equal to the second diameter.

8. The fiber tip fluid output device as set forth in claim 7, wherein:
the proximal lumen section comprises a proximal end, a distal end, and a lumen axis extending between the proximal end and the distal end;
the distal lumen section comprises a proximal end, a distal end, and a lumen axis extending between the proximal end and the distal end;
the diameter of the proximal lumen section is substantially constant along a length of the proximal lumen section between the proximal end of the proximal lumen section and the distal end of the proximal lumen section; and
the diameter of the distal lumen section is substantially constant along a length of the distal lumen section between the proximal end of the distal lumen section and the distal end of the distal lumen section.

9. The fiber tip fluid output device as set forth in claim 8, where the first diameter transitions to the second diameter at the distal end of the proximal lumen section and the proximal end of the distal lumen section.

10. The fiber tip fluid output device as set forth in claim 8, wherein the plurality of apertures comprises four apertures.

11. The fiber tip fluid output device as set forth in claim 10, wherein the four apertures are evenly spaced on the depression.

12. The fiber tip fluid output device as set forth in claim 11, wherein a distal opening of the fiber tip fluid output device has a diameter which is equal to the second diameter and a proximal opening of the fiber tip fluid output device has a diameter which is equal to the first diameter.

13. The fiber tip fluid output device as set forth in claim 11, wherein each of the four apertures has a circular opening.

14. The fiber tip fluid output device as set forth in claim 13, wherein each aperture has a diameter which is about half of the first diameter.

15. The fiber tip fluid output device as set forth in claim 13, wherein the depression comprises a first depression and wherein the fiber tip fluid output device further comprises:
a second depression extending around the generally cylindrical body near the proximal end; and
a third depression extending around the generally cylindrical body near the distal end.

16. The fiber tip fluid output device as set forth in claim 15, wherein the first depression is disposed about half way between the second depression and the third depression.

17. A loading tool, comprising:
a cylindrical body having a proximal end, a distal end, and an axis extending between the proximal end and the distal end;
a slot for accommodating the fiber tip fluid output device of claim 15, the slot being disposed within the cylindrical body and having a width, measured in a direction transverse to the axis, which is approximately equal to a depression diameter of the fiber tip fluid output device, the depression diameter of the fiber tip fluid output device being defined as a diameter of the fiber tip fluid output device measured within the third depression, whereby the third depression of the fiber tip fluid output device can be advanced into the slot of the loading tool to thereby allow the loading tool to hold the fiber tip fluid output device for loading into a laser handpiece.

18. The loading tool as set forth in claim 17, wherein:
the fiber tip fluid output device has a non-depression diameter which is defined as a diameter of the fiber tip fluid output device at a point along the fiber tip fluid output device which is adjacent to the third depression; and
the width of the slot is greater than the depression diameter.

19. A method of using a loading tool to connect a fiber tip fluid output device to a laser handpiece, the method comprising the following steps:

providing a loading tool having cylindrical body with a proximal end, a distal end, an axis extending between the proximal end and the distal end, and a slot constructed to accommodate the fiber tip fluid output device of claim 15;

positioning the fiber tip fluid output device within the slot;

using the loading tool to place the fiber tip fluid output device into an aperture disposed within the laser handpiece, while the fiber tip fluid output device is within the slot; and removing the loading tool from the fiber tip fluid output device to thereby leave the fiber tip fluid output device positioned within the aperture of the laser handpiece.

20. The method according to claim 19, wherein the slot is disposed within the cylindrical body and extends in a direction from the proximal end to the distal end, the slot having a width, which is approximately equal to a depression diameter of the fiber tip fluid output device, the depression diameter of the fiber tip fluid output device being defined as a diameter of the fiber tip fluid output device measured within the third depression, the third depression of the fiber tip fluid output device being advanced into the slot of the loading tool to thereby allow the loading tool to hold the fiber tip fluid output device for loading into the aperture of the laser handpiece.

21. The fiber tip fluid output device as set forth in claim 13, wherein the plurality of apertures are spaced about half way between the proximal end and the distal end.

22. The fiber tip fluid output device as set forth in claim 7, wherein each of the plurality of apertures has a cross-sectional diameter, and wherein the distal lumen section tapers into the proximal lumen section along a length of the lumen that is equal to about one third of at least one of the cross-sectional diameters.

23. The fiber tip fluid output device as set forth in claim 7, wherein at least one of the plurality of apertures facilitates an entry of fluids therethrough and into the distal lumen section, and the distal lumen section is adapted to output water particles onto a fiber tip extending through the fiber tip fluid output device.

24. The fiber tip fluid output device as set forth in claim 2, wherein the depression comprises a ring shape and extends around a minimum circumference of the fiber tip fluid output device.

25. The fiber tip fluid output device as set forth in claim 2, wherein the depression serves, as a mixing chamber for mixing air and water together when the fiber tip fluid output device is connected to the electromagnetic energy cutting apparatus.

26. The fiber tip fluid output device as set forth in claim 2, wherein the depression serves as a mixing chamber for mixing air and medicated or flavored water together when the fiber tip fluid output device is connected to the electromagnetic energy cutting apparatus.

27. The fiber tip fluid output device as set forth in claim 2, wherein the depression serves as a mixing chamber for mixing water with at least one other fluid.

28. The fiber tip fluid output device as set forth in claim 27, wherein the at least one other fluid comprises a medicament.

29. The fiber tip fluid output device as set forth in claim 28, wherein the medicament comprises chlorhexidine gluconate.

30. The fiber tip fluid output device as set forth in claim 27, wherein the plurality of apertures comprises four apertures.

31. The fiber tip fluid output device as set forth in claim 30, wherein the four apertures are evenly spaced on the depression.

32. The fiber tip fluid output device as set forth in claim 30, wherein each of the four apertures comprises a circular opening.

33. The fiber tip fluid output device as set forth in claim 32, wherein the depression comprises a first depression and wherein the fiber tip fluid output device further comprises:

a second depression extending around the generally cylindrical body near the proximal end; and a third depression extending around the generally cylindrical body near the distal end.

34. The fiber tip fluid output device as set forth in claim 33, wherein the first depression is disposed about half way between the second depression and the third depression.

35. The fiber tip fluid output device as set forth in claim 32, wherein the plurality of apertures are spaced about half way between the proximal end and the distal end.

36. The fiber tip fluid output device as set forth in claim 2, wherein the mixing chamber mixes air and water to create atomized water particles.

37. The fiber tip fluid output device as set forth in claim 2, wherein the mixing chamber is constructed to mix fluids together and to output atomized fluid particles onto a fiber tip extending through the fiber tip fluid output device.

38. The fiber tip fluid output device as set forth in claim 2, and further comprising a fiber tip permanently affixed to and extending through the fiber tip fluid output device.

39. The fiber tip fluid output device as set forth in claim 1, wherein the plurality of apertures extend around the generally cylindrical body in a ring-like fashion.

40. A fiber tip fluid output device for holding a fiber tip in an electromagnetic energy cutting apparatus and for directing water particles over a radiation delivery end of the fiber tip, the fiber tip fluid output device comprising:

a generally cylindrical body having an outer surface, a proximal end, a distal end, and a lumen extending between the proximal end and the distal end, the lumen being sized and shaped to accommodate a fiber tip therein so that the fiber tip extends through the lumen from the proximal end to the distal end of the generally cylindrical body;

a depression disposed in the outer surface of the generally cylindrical body, the depression extending around the generally cylindrical body and serving as a mixing chamber for mixing fluids together when the fiber tip fluid output device is connected to the electromagnetic energy cutting apparatus; and at least one aperture disposed in the depression, the at least one aperture fluidly connecting the outer surface to the lumen.

41. The fiber tip fluid output device as set forth in claim 40, wherein the at least one aperture comprises a plurality of apertures.

42. The fiber tip fluid output device as set forth in claim 40, wherein the depression serves as a mixing chamber for mixing air with one of a medicament or flavoring agent when the fiber tip fluid output device is connected to the electromagnetic energy cutting apparatus.

43. A method of outputting fluid onto a fiber tip of an electromagnetic energy cutting apparatus, comprising the following steps:

providing a fiber tip fluid output device, the fiber tip fluid output device having a proximal end, a distal end, and a lumen extending between the proximal end and the distal end, whereby the fiber tip extends through the lumen of the fiber tip fluid output device and extends distally out of the distal end of the fiber tip fluid output device;

routing at least two fluids circumferentially around the fiber tip fluid output device, to thereby mix the two fluids;

inputting the two fluids into the lumen; and outputting the two fluids from the lumen out of the distal end of the fiber tip fluid output device.

44. The method of outputting fluid onto a fiber tip of an electromagnetic energy cutting apparatus according to claim 43, the two fluids being output as atomized fluid particles onto the fiber tip.

45. The method of outputting fluid onto a fiber tip of an electromagnetic energy cutting apparatus according to claim 43, wherein:

the step of routing at least two fluids circumferentially around the fiber tip fluid output device comprises a step of routing at least two fluids circumferentially within a circumferential depression disposed on the fiber tip fluid output device; and the step of inputting the two fluids into the lumen is followed by a step of further mixing the two fluids within the lumen.

46. The method of outputting fluid onto a fiber tip of an electromagnetic energy cutting apparatus according to claim 45, wherein the two fluids are output as atomized fluid particles.

47. The method of outputting fluid onto a fiber tip of an electromagnetic energy cutting apparatus according to claim 45, wherein the step of inputting the two fluids into the lumen comprises a step of inputting the two fluids through a plurality of apertures of the fiber tip fluid output device and into the lumen.

48. The method of outputting fluid onto a fiber tip of an electromagnetic energy cutting apparatus according to claim 47, wherein the step of routing at least two fluids circumferentially around the fiber tip fluid output device comprises a step of mixing air with one of a medicament or flavoring agent.

49. The method of outputting fluid onto a fiber tip of an electromagnetic energy cutting apparatus according to claim 47, wherein the step of routing at least two fluids circumferentially around the fiber tip fluid output device comprises a step of mixing pressurized air and water.

50. The method of outputting fluid onto a fiber tip of an electromagnetic energy cutting apparatus according to claim 47, wherein the step of routing at least two fluids circumferentially around the fiber tip fluid output device comprises a step of mixing water with at least one of a medicament and a flavoring.

51. The method of outputting fluid onto a fiber tip of an electromagnetic energy cutting apparatus according to claim 47, wherein the step of routing at least two fluids circumferentially around the fiber tip fluid output device comprises a step of mixing water with at least one other fluid.

52. The method of outputting fluid onto a fiber tip of an electromagnetic energy cutting apparatus according to claim 51, wherein the at least one other fluid comprises a medicament.

53. The method of outputting fluid onto a fiber tip of an electromagnetic energy cutting apparatus according to claim 52, wherein the medicament comprises chlorhexidine gluconate.

* * * * *

UNITED STATES PATENT AND TRADEMARK OFFICE
CERTIFICATE OF CORRECTION

PATENT NO.     : 6,567,582 B1                                                    Page 1 of 1
DATED          : May 20, 2003
INVENTOR(S)    : Rizoiu et al.

It is certified that error appears in the above-identified patent and that said Letters Patent is hereby corrected as shown below:

<u>Title page,</u>
Item [73], should read:
-- Assignee: BioLase Technology, Inc. San Clemente, CA (US) --
Item [74], should read:
-- *Attorney, Agent, or Firm*-Stout, Uxa, Buyan & Mullins, LLP --

<u>Column 3,</u>
Line 61, "also comprise molypdium" should read -- also comprise molybdenum --

Signed and Sealed this

Twenty-fifth Day of May, 2004

JON W. DUDAS
*Acting Director of the United States Patent and Trademark Office*